US011878106B2

(12) United States Patent
Ingram et al.

(10) Patent No.: US 11,878,106 B2
(45) Date of Patent: *Jan. 23, 2024

(54) SYSTEM AND METHODS FOR THE TREATMENT OF WOUNDS WITH NEGATIVE PRESSURE AND INSTILLATION OF PEROXIDE PYRUVIC ACID

(71) Applicant: KCI Licensing, Inc., San Antonio, TX (US)

(72) Inventors: Shannon C. Ingram, Bulverde, TX (US); Christopher A. Carroll, San Antonio, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 51 days.

This patent is subject to a terminal disclaimer.

(21) Appl. No.: 16/822,306

(22) Filed: Mar. 18, 2020

(65) Prior Publication Data

US 2020/0306428 A1    Oct. 1, 2020
US 2023/0148444 A9    May 11, 2023

Related U.S. Application Data

(63) Continuation-in-part of application No. 15/392,232, filed on Dec. 28, 2016, now Pat. No. 11,259,528.
(Continued)

(51) Int. Cl.
*A61M 1/00* (2006.01)
*A61F 13/00* (2006.01)
*A61K 31/327* (2006.01)

(52) U.S. Cl.
CPC ......... *A61M 1/85* (2021.05); *A61F 13/00017* (2013.01); *A61F 13/00063* (2013.01);
(Continued)

(58) Field of Classification Search
CPC .. A61M 1/85; A61M 1/90; A61M 2205/3344; A61M 2205/50;
(Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

International Search Report and Written Opinion for Corresponding Application No. PCT/US2020/023327, dated Aug. 17, 2020.
(Continued)

*Primary Examiner* — Kai H Weng
*Assistant Examiner* — Nhu Q. Tran (57) ABSTRACT

In one example embodiment, a system for treating a tissue site is disclosed comprising a dressing adapted to contact the tissue site and provide a fluid seal between a therapeutic environment and a local external environment, and a solution source fluidly coupled to the dressing and adapted to deliver an antimicrobial solution comprising a peroxy α-keto carboxylic acid, such as peroxy pyruvic acid, to the tissue interface. The system may further comprise a negative-pressure source fluidly coupled to the dressing and adapted to provide negative pressure to the therapeutic environment after delivery of the antimicrobial fluid to the therapeutic environment. In another example embodiment, a method for treating a tissue site is disclosed comprising positioning a tissue interface to contact the tissue site, covering the tissue interface and the tissue site with a drape
(Continued)

to provide a fluid seal between the therapeutic environment and the local external environment, and delivering an antimicrobial solution comprising peroxy α-keto carboxylic acid to the therapeutic environment before providing negative pressure to the therapeutic environment.

15 Claims, 4 Drawing Sheets

Related U.S. Application Data (60) Provisional application No. 62/824,813, filed on Mar. 27, 2019, provisional application No. 62/272,529, filed on Dec. 29, 2015.

(52) U.S. Cl.
CPC ...... *A61F 13/00068* (2013.01); *A61K 31/327* (2013.01); *A61M 1/92* (2021.05); *A61M 1/96* (2021.05); *A61M 2205/18* (2013.01); *A61M 2205/3344* (2013.01); *A61M 2205/50* (2013.01); *A61M 2205/502* (2013.01); *A61M 2205/52* (2013.01)

(58) Field of Classification Search
CPC ........ A61M 2205/18; A61M 2205/502; A61M 2205/52; A61F 13/00017; A61F 13/00063; A61F 13/00068; A61K 31/327
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Denbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

(56) References Cited

U.S. PATENT DOCUMENTS

| | | | |
|---|---|---|---|
| 2006/0100594 A1* | 5/2006 | Adams | A61M 1/84 604/313 |
| 2010/0298792 A1* | 11/2010 | Weston | A61M 1/74 604/319 |
| 2012/0213835 A1* | 8/2012 | Neas | A61P 17/02 514/557 |
| 2013/0178785 A1 | 7/2013 | Papay et al. | |
| 2013/0211348 A1* | 8/2013 | Randolph | A61F 13/00068 604/290 |
| 2014/0163491 A1 | 6/2014 | Schuessler et al. | |
| 2015/0080788 A1 | 3/2015 | Blott et al. | |
| 2016/0015873 A1* | 1/2016 | Robinson | A61M 3/0212 604/315 |
| 2017/0182230 A1 | 6/2017 | Ingram et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 0100148 A1 | 2/1984 |
| DE | 43 06 478 A1 | 9/1994 |
| DE | 29 504 378 U1 | 9/1995 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 1129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 pages English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, p. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, " Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All—Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. @ Therapy Clinical Guidelines: A Reference Source for Clinicians; Jul. 2007.

* cited by examiner

SYSTEM AND METHODS FOR THE TREATMENT OF WOUNDS WITH NEGATIVE PRESSURE AND INSTILLATION OF PEROXIDE PYRUVIC ACID

RELATED APPLICATIONS

This application claims the benefit, under 35 U.S.C. § 119(e), of the filing of U.S. Provisional Patent Application Ser. No. 62/824,813, entitled "SYSTEM AND METHODS FOR THE TREATMENT OF WOUNDS WITH NEGATIVE PRESSURE AND INSTILLATION OF PEROXIDE PYRUVIC ACID," filed Mar. 27, 2019, which is incorporated herein by reference for all purposes. This application is also a continuation-in-part of U.S. patent application Ser. No. 15/932,232, entitled "System and Methods for Treatment of Wounds with Negative Pressure and Peroxy Pyruvic Acid," filed Dec. 28, 2016, issued as U.S. Pat. No. 11,259,528, which claims the benefit of U.S. Provisional Application No. 62/272,529, filed on Dec. 29, 2015.

TECHNICAL FIELD

The invention set forth in the appended claims relates generally to tissue treatment systems and more particularly, but without limitation, to treating wounds with negative pressure and instillation of an antimicrobial solution in a negative-pressure and instillation therapy environment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, there is an ongoing need to develop improved therapy systems, components, and processes.

BRIEF SUMMARY

New and useful systems, apparatuses, and methods for treating wounds with negative pressure and instillation of an antimicrobial solution comprising a peroxy α-keto carboxylic acid, such as peroxy pyruvic acid, in a negative-pressure and instillation therapy environment are set forth in the appended claims. Illustrative embodiments are also provided to enable a person skilled in the art to make and use the claimed subject matter.

For example, in some embodiments, instillation and negative pressure therapy systems and methods are especially effective for improving tissue granulation when used in conjunction with antimicrobial solutions of the present technology that have demonstrated efficacy against a broad range of healthcare-associated infections (HAIs), biofilms and planktonic microbes that are categorized and described below. To combat the growing threat of infections, antimicrobial solutions may be used as an installation fluid in conjunction with the automated instillation and negative pressure therapy systems and methods described herein. For example, without limiting the mechanism, function or utility of present technology, it has been found that antimicrobial solutions comprising peroxy pyruvic acid have demonstrated unique safety and efficacy properties that can mitigate or treat the increasing threat of HIAs, including the most resistant pathogens such as methicillin resistant *Staphylococcus aureus* (MRSA), CRE and *C. difficile* spores.

More specifically, in one example embodiment, a system for treating a tissue site comprising a dressing adapted to contact the tissue site and provide a fluid seal between a therapeutic environment and a local external environment, and a solution source fluidly coupled to the dressing and adapted to deliver an antimicrobial solution comprising a peroxy pyruvic acid to the tissue interface is disclosed. The system may further comprise a negative-pressure source fluidly coupled to the dressing and adapted to provide negative pressure to the therapeutic environment after delivery of the antimicrobial fluid to the therapeutic environment. The system may further comprise a positive-pressure source fluidly coupled to the solution source and adapted to actuate the solution source for delivering the antimicrobial solution to the therapeutic environment and the tissue site. The system may further comprise a processor operatively coupled to the negative-pressure source and the positive-pressure source to provide negative pressure to the therapeutic environment in pressure control modes after or during the time period that the antimicrobial solution is provided to the therapeutic environment.

Alternatively, in another example embodiment, a method for treating a tissue site is disclosed comprising positioning a tissue interface to contact the tissue site, covering the tissue interface and the tissue site with a drape to provide a fluid seal between the therapeutic environment and the local external environment, and delivering an antimicrobial solution comprising an antimicrobial agent containing peroxy α-keto carboxylic acid (e.g., peroxy pyruvic acid) the therapeutic environment before providing negative pressure to the therapeutic environment. The method may further comprise a providing negative pressure to the therapeutic environment in pressure control modes after or during the time period that the antimicrobial solution is provided to the therapeutic environment.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the technology.

The present technology provides solutions comprising a peroxy α-keto carboxylic acid ("antimicrobial solutions") for use in a negative pressure treatment regime. Such peroxy α-keto carboxylic acids include peroxyacids of the general formula wherein R is alkyl, such as $C_1$-$C_5$ alkyl. In various embodiments, antimicrobial solutions comprise a peroxy α-keto carboxylic acid selected from the group consisting of peroxy puryvic acid, peroxy α-keto butyric acid, peroxy α-keto valeric acid, and mixtures thereof. A preferred α-keto carboxylic acid is peroxy peruvic acid. Peroxy α-keto carboxylic acids among those useful herein are disclosed in U.S. Pat. No. 8,426,634, Neas et al., issued Apr. 23, 2013; U.S. Pat. No. 8,445,717, Neas, et al., issued May 21, 2013; and U.S. Patent Application Publication 2012.0213835, Neas et al., published Aug. 23, 2012, the disclosures of which regarding peroxy α-keto carboxylic acids and their synthesis are incorporated by reference herein.

Antimicrobial solutions of the present technology may comprise pharmaceutically acceptable carriers, optional active materials, and excipients. As used herein, such a "pharmaceutically acceptable" component is one that is suitable for use with humans and/or animals without undue adverse side effects (such as toxicity, irritation, and allergic response) commensurate with a reasonable benefit/risk ratio. Preferably, the antimicrobial solutions comprise a pharmaceutically acceptable carrier, such as water or physiological saline. In general, the peroxy α-keto carboxylic acid is present in the antimicrobial solution at a level of from about 5,000 ppm or less.

In various embodiments, the antimicrobial solution comprises an aqueous solution of peroxy pyruvic acid at a concentration of from about 5% to about 0.001% (by weight). For example, the peroxy pyruvic acid about 5% or less, about 2% or less, about 1% or less, about 0.8% or less, about 0.5% or less, about 0.4% or less, about 0.2% or less, about 0.1% or less, about 0.07% or less, about 0.05% or less, or about 0.04% or less, about 0.03% or less, or about 0.01% or less, or about 0.005% or less, or about 0.002% or less. For example, in some embodiments the peroxy pyruvic acid concentration may be about 0.04%, about 0.1%, or about 0.15%, or about 0.25%. Expressed as parts per million (ppm), the concentration of peroxy pyruvic acid may be from about 10 ppm to about 12000 ppm, about 50 ppm to about 5000 ppm, or from about 100 ppm to about 4000 ppm, or from about 400 ppm to about 3500 ppm, or from about 500 ppm to about 1500 ppm. For example, in various embodiments, the concentration of peroxy pyruvic acid is about 50 ppm, about 100 ppm, about 300 ppm, about 400 ppm, about 1000 ppm, about 1500 ppm, about 2500 ppm, about 3500 ppm, about 4000 ppm, about 8000 ppm or about 12000 ppm. In various embodiments, the molarity of peroxy pyruvic acid may be from about 0.01 mM to about 1 M, from about 1 mM to about 0.5 M, or from about 10 mM to about 250 mM. In one embodiment, the concentration is about 0.04% or about 400 ppm.

In some embodiments, the antimicrobial solution comprises peroxy pyruvic acid, pyruvic acid and hydrogen peroxide. In one embodiment, the antimicrobial solution is, or comprises, the VERIOX™ antimicrobial agent, comprising peroxy pyruvic acid, available from CHD Bioscience of Fort Collins, Colorado.

In some embodiments, the antimicrobial solution comprises one or more optional antimicrobial agents, such as hypochlorite, silver nitrate, sulfur-based based antimicrobials, biguanides, and cationic antimicrobials. In some embodiments, the antimicrobial solution comprises an α-keto ester, preferably an alkyl α-keto ester such as an alkyl pyruvate ester. Such esters and compositions are described in U.S. Patent Application Publication 2012.0213835, Neas et a., published Aug. 23, 2012, the disclosure of which regarding such esters and compositions are incorporated by reference herein.

Figure 1:
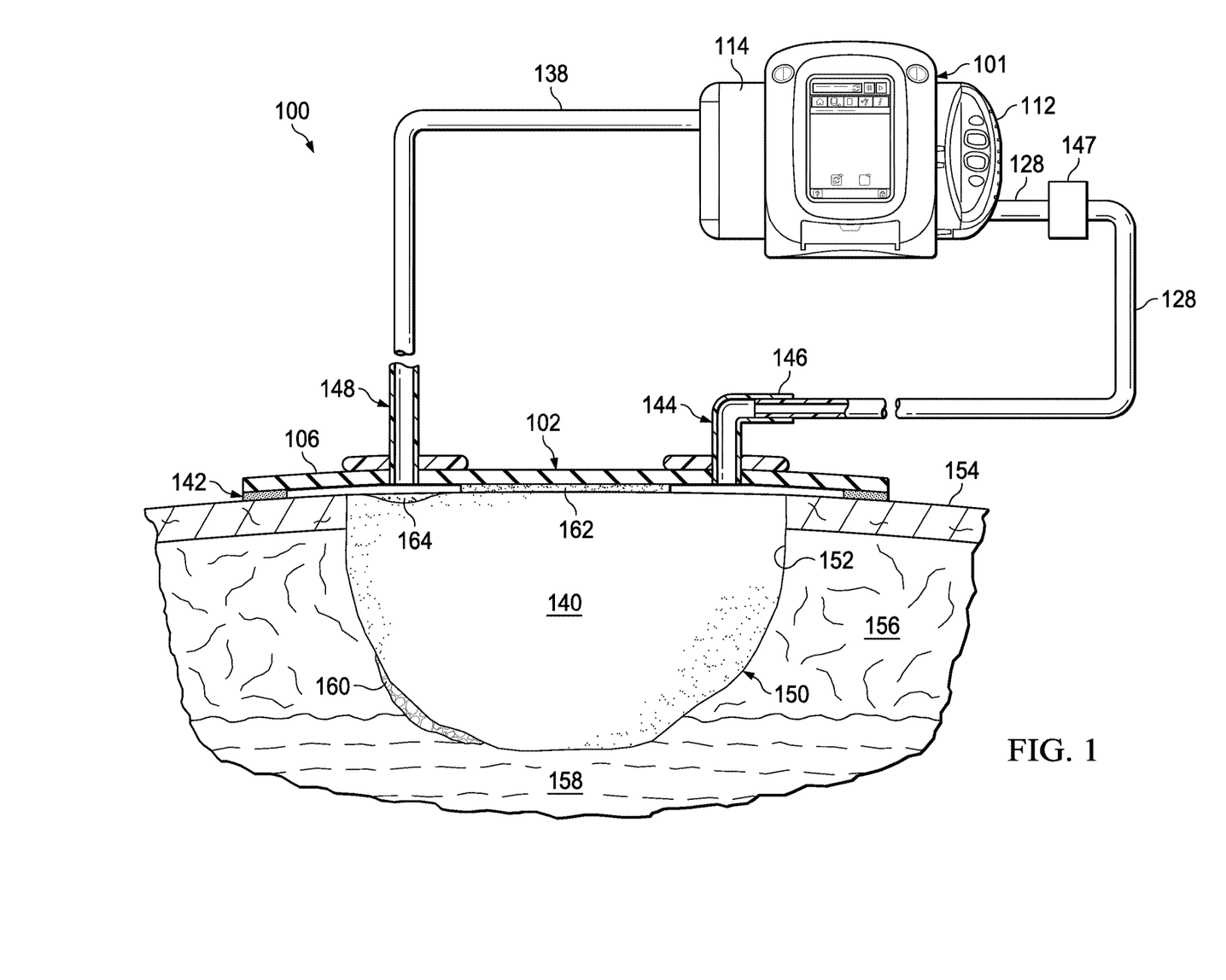
FIG. 1 is a schematic diagram of an example embodiment of a negative-pressure and instillation therapy system for delivering treatment solutions to a dressing at a tissue site.
Figure 1A:
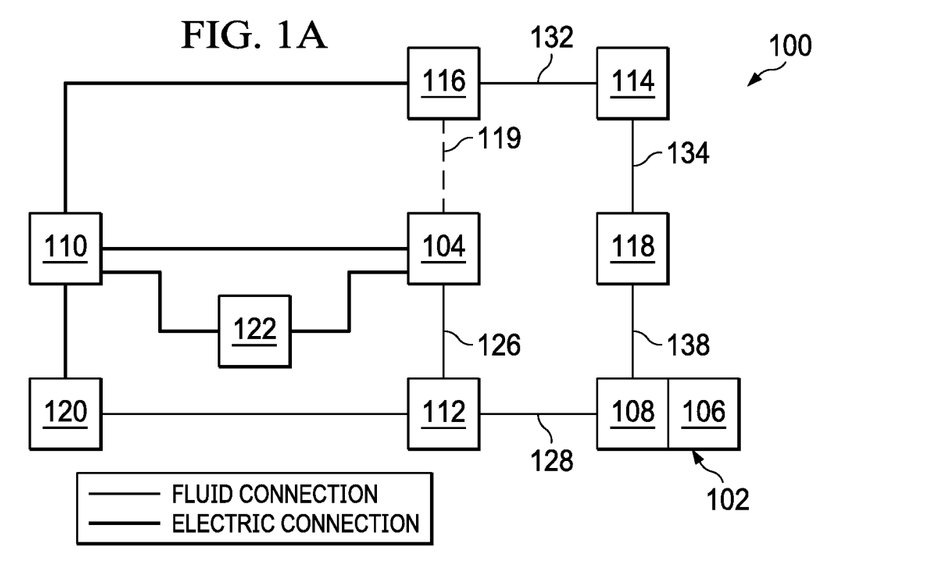
FIG. 1A is a functional block diagram of an example embodiment of a therapy system of FIG. 1 that can deliver treatment solutions in accordance with this specification.

The present technology also provides negative pressure therapy devices and systems, and methods of treatment using such systems with antimicrobial solutions. FIG. 1 is a schematic diagram of an example embodiment of a negative-pressure and instillation therapy system for delivering treatment solutions to a dressing at a tissue site. FIG. 1A is a simplified functional block diagram of an example embodiment of a therapy system 100 that can provide negative-pressure therapy with instillation of treatment solutions in accordance with this specification. The therapy system 100 may be packaged as a single, integrated unit such as therapy system 101. The therapy system 101 may be, for example, a V.A.C. Ulta™ System available from Kinetic Concepts, Inc. of San Antonio, Texas.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1A. A dressing may include a cover, a tissue interface, or both in some embodiments. The dressing 102, for example, may include a cover 106 and a tissue interface 108. A regulator or a controller, such as a controller 110, may also be coupled to the negative-pressure source 104. The therapy system 100 may optionally include a fluid container, such as a container 112, coupled to the dressing 102 and to the negative-pressure source 104.

The therapy system 100 may also include a source of instillation solution. For example, a solution source 114 may be fluidly coupled to the dressing 102, as illustrated in the example embodiment of FIG. 1. The solution source 114 may be fluidly coupled to a positive-pressure source such as the positive-pressure source 116 in some embodiments, or may be fluidly coupled to the negative-pressure source 104. A regulator, such as an instillation regulator 118, may also be fluidly coupled to the solution source 114 and the dressing 102. In some embodiments, the instillation regulator 118 may also be fluidly coupled to the negative-pressure source 104 through the dressing 102, as illustrated in the example of FIG. 1. In some embodiments, the negative-pressure source 104 and the positive-pressure source 116 may be a single pressure source or unit as indicated by dashed line 119.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122, or both, coupled to the controller 110. The pressure sensor 120 may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the tissue interface 108 of the dressing 102 through the container 112 by conduits 126 and 128. Additionally, the positive-pressure source 116 may be directly coupled to the controller 110, and may be indirectly coupled to the tissue interface 108 through the solution source 114 and the instillation regulator 118 by conduits 132, 134 and 138.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit, such as therapy system 101. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold 140. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source.

In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Texas.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced (i.e., below ambient pressure). For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device, such as an attachment device 142, may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, a dressing interface may facilitate coupling the negative pressure source 104 to the dressing 102. The negative pressure provided by the negative-pressure source 104 may be delivered through the conduit 128 to a negative-pressure interface 144, which may include an elbow port 146. In one illustrative embodiment, the negative-pressure interface 144 is a T.R.A.C.® Pad or Sensa T.R.A.C.® Pad available from KCl of San Antonio, Texas. The negative-pressure interface 144 allows the negative pressure to be delivered to the cover 106 and realized within an interior portion of the cover 106 and the manifold 140. In this illustrative, non-limiting embodiment, the elbow port 146 extends through the cover 106 to the manifold 140, but numerous arrangements are possible.

The therapy system 100 may also include a particulate filter 147, which may be positioned in fluid communication between the fluid container 112 and/or the negative-pressure source 104 and the dressing 102. The particulate filter 147 may function to remove particulate matter from the effluent that has circulated through the dressing 102. For example, fluid delivered to the dressing 102 and to a tissue site may be drawn out of the dressing 102 through the negative-pressure interface 144 and transported through negative-pressure conduit 128 to the particulate filter 147. The fluid may be filtered to remove particulate matter in the particulate filter 147, before being recollected in the fluid container 112.

The therapy system 100 may also include a second interface that may facilitate coupling of the positive-pressure source 116 to the dressing 102, such as fluid-delivery interface 148. The positive pressure provided by the positive-pressure source 116 may be delivered through the conduit 138. The fluid-delivery interface 148 also may be fluidly coupled to the dressing 102 and may pass through a hole cut in the cover 106. The hole cut in the cover 106 for the fluid-delivery interface 148 may be separated as far apart as possible from its location or other hole cut in the cover 106 through which the negative-pressure interface 144 may pass. The fluid-delivery interface 148 may allow for a fluid, such as an antimicrobial solution of the present technology, to be delivered by the therapy system 100 through the cover 106 and to the manifold 140. In some embodiments, the fluid-delivery interface 148 may include an inlet pad. The inlet pad may be a non-dampening material or a material that is not sound-absorbing. In some embodiments, the inlet pad may be an elastomer. For example, the inlet pad may be an elastic polymer, such as polyurethane, thermoplastic elastomers, polyether block amide (PEBAX), polyisoprene, polychloroprene, chlorosulphonated polythene, and polyisobutylene, blends and copolymers. In one illustrative embodiment, the fluid-delivery interface 148 and the negative-pressure interface 144 may be integrated into a single pad for the delivery and removal of solutions from the tissue site 150, such as a V.A.C. Vera T.R.A.C.™ Pad available from Kinetic Concepts, Inc. of San Antonio, Texas.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy, such as an antimicrobial solution of the present technology. As discussed above, the compositions of the antimicrobial solutions may vary according to a prescribed therapy, comprising optional antmicrobial actives in addition to a peroxy α-keto carboxylic acid. In some embodiments, methods of the present technology employ only (consist essentially of administering) an antimicrobial solution comprising peroxy puryvic acid or other peroxy α-keto carboxylic acid. In other embodiments, methods may further comprise administration of other therapeutic solutions. Examples of such other therapeutic solutions that may be suitable for some prescriptions include hypochlorite-based solutions, silver nitrate (0.5%), sulfur-based solutions, biguanides, cationic solutions, and isotonic solutions. In one illustrative embodiment, the solution source 114 may include a storage component for the solution and a separate cassette for holding the storage component and delivering the solution to the tissue site 150, such as a V.A.C. VeraLink™ Cassette available from Kinetic Concepts, Inc. of San Antonio, Texas.

In operation, the tissue interface 108 may be placed within, over, on, or otherwise proximate to a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

As discussed above, the tissue site 150 may include, without limitation, any irregularity with a tissue, such as an open wound, surgical incision, or diseased tissue. The therapy system 100 is presented in the context of a tissue site that includes a wound 152, which is through the epidermis 154, or generally skin, and the dermis 156 and reaching into a hypodermis, or subcutaneous tissue 158. The therapy system 100 may be used to treat a wound of any depth, as well as many different types of wounds including open wounds or other tissue sites. The tissue site 150 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 150 may include removal of fluids originating from the tissue site 150, such as exudates or ascites, or fluids instilled into the dressing to cleanse or treat the tissue site 150, such as antimicrobial solutions. The wound 152 may include undesirable tissue 160, biofilm 162 formed on any living or nonliving surface of the dressing 102 or the tissue site 150, and planktonic microbes 164 floating or swimming in liquid medium in and around the dressing 102. Such undesirable tissue may include, necrotic, damaged, infected, contaminated, or adherent tissue, foreign material within the wound 152. In many instances, it may be desirable to remove the undesirable tissue 160 or treat the biofilm 162 and planktonic microbes 164 with antimicrobials in order to promote healing of the wound 152. The illustrative, non-limiting embodiment shows the therapy system 100 in the context of the wound 152 and the tissue site 150 having a localized discrete area of undesirable tissue 160, biofilm 162, or planktonic microbes 164 within the wound 152. The therapy system 100 may be used in broader contexts, including with any type of tissue site including wounds, defects, or other treatment target located on or within living or nonliving tissue.

In one embodiment, controller 110 receives and processes data, such as data related to the pressure distributed to the tissue interface 108 from the pressure sensor 120. The controller 110 may also control the operation of one or more components of therapy system 100 to manage the pressure distributed to the tissue interface 108 for application to the wound 152 at the tissue site 150, which may also be referred to as the wound pressure (WP). In one embodiment, controller 170 may include an input for receiving a desired target pressure (TP) set by a clinician or other user and may be program for processing data relating to the setting and inputting of the target pressure (TP) to be applied to the tissue site 150. In one example embodiment, the target pressure (TP) may be a fixed pressure value determined by a user/caregiver as the reduced pressure target desired for therapy at the tissue site 150 and then provided as input to the controller 110. The user may be a nurse or a doctor or other approved clinician who prescribes the desired negative pressure to which the tissue site 150 should be applied. The desired negative pressure may vary from tissue site to tissue site based on the type of tissue forming the tissue site 150, the type of injury or wound 152 (if any), the medical condition of the patient, and the preference of the attending physician. After selecting the desired target pressure (TP), the negative pressure source 104 is controlled to achieve the target pressure (TP) desired for application to the tissue site 150.

Figure 2A:
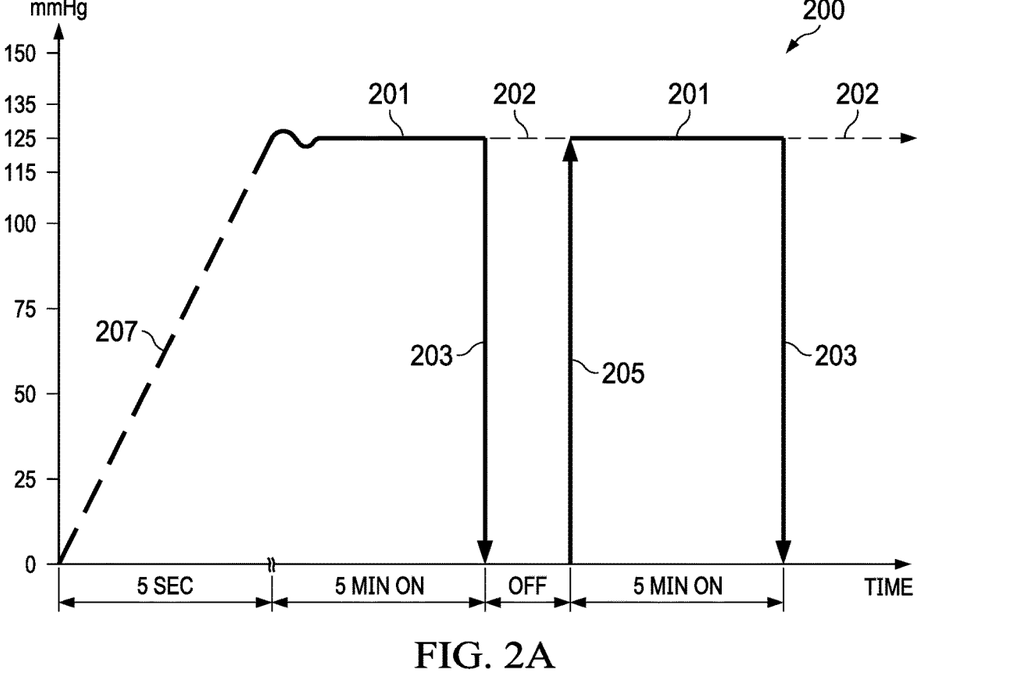
FIG. 2A is a graph illustrating an illustrative embodiment of pressure control modes for the negative-pressure and instillation therapy system of FIGS. 1 and 1A wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system.

Referring more specifically to FIG. 2A, a graph illustrating an illustrative embodiment of pressure control modes 200 that may be used for the negative-pressure and instillation therapy system of FIGS. 1 and 1A is shown wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system. The target pressure (TP) may be set by the user in a continuous pressure mode as indicated by solid line 201 and dotted line 202 wherein the wound pressure (WP) is applied to the tissue site 150 until the user deactivates the negative pressure source 104. The target pressure (TP) may also be set by the user in an intermittent pressure mode as indicated by solid lines 201, 203 and 205 wherein the wound pressure (WP) is cycled between the target pressure (TP) and atmospheric pressure. For example, the target pressure (TP) may be set by the user at 125 mmHg below ambient pressure for a specified period of time (e.g., 5 min) followed by the therapy being turned off for a specified period of time (e.g., 2 min) as indicated by lines 203 by venting the tissue site 150 to the atmosphere, and then repeating the cycle by turning the therapy back on as indicated by line 205 which consequently forms a square wave pattern between the target pressure (TP) level and no pressure. In various embodiments the steps of providing negative pressure and providing the antimicrobial solution are sequentially repeated two or more times.

The decrease of the wound pressure (WP) at the tissue site 150 from ambient pressure to the target pressure (TP) is not instantaneous, but rather gradual depending on the type of therapy equipment and the dressing. For example, the negative pressure source 104 and the dressing 102 may have an initial rise time as indicated by the dashed line 207 that may vary depending on the type of dressing and therapy equipment being used. For example, the initial rise time for one therapy system may be in the range between about 20-30 mmHg/second or, more specifically, equal to about 25 mmHg/second, and in the range between about 5-10 mmHg/second for another therapy system. When the therapy system 100 is operating in the intermittent mode, the repeating rise time 205 may be a value substantially equal to the initial rise time 207.

The target pressure may also be a variable target pressure (VTP) controlled or determined by controller 110 that varies in a dynamic pressure mode. For example, the variable target pressure (VTP) may vary between a maximum and minimum pressure value that may be set as an input determined by a user as the range of negative pressures desired for therapy at the tissue site 150. The variable target pressure (VTP) may also be processed and controlled by controller 110 that varies the target pressure (TP) according to a predetermined waveform such as, for example, a sine waveform or a saw-tooth waveform or a triangular waveform, that may be set as an input by a user as the predetermined or time-varying reduced pressures desired for therapy at the tissue site 150.

Figure 2B:
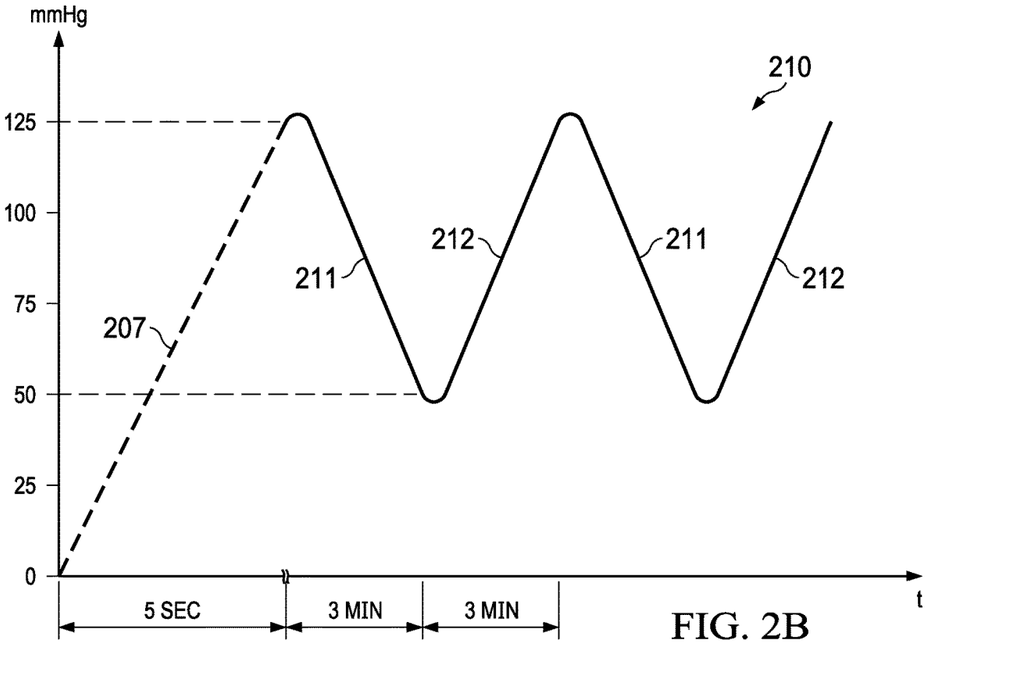
FIG. 2B is a graph illustrating an illustrative embodiment of another pressure control mode for the negative-pressure and instillation therapy system of FIGS. 1 and 1A wherein the x-axis represents time in minutes (min) and/or seconds (sec) and the y-axis represents pressure generated by a pump in Torr (mmHg) that varies with time in a dynamic pressure mode that may be used for applying negative pressure in the therapy system.

Referring more specifically to FIG. 2B, a graph illustrating an illustrative embodiment of another pressure control mode for the negative-pressure and instillation therapy system of FIGS. 1 and 1A is shown wherein the x-axis represents time in minutes (min) and/or seconds (sec) and the y-axis represents pressure generated by a pump in Torr (mmHg) that varies with time in a dynamic pressure mode that may be used for applying negative pressure (i.e., reduced pressure, below ambient pressure) in the therapy system. For example, the variable target pressure (VTP) may be a reduced pressure that provides an effective treatment by applying reduced pressure to tissue site 150 in the form of a triangular waveform varying between a minimum and maximum pressure of 50-125 mmHg below ambient pressure with a rise time 212 set at a rate of +25 mmHg/min. and a descent time 211 set at −25 mmHg/min, respectively. In another embodiment of the therapy system 100, the variable target pressure (VTP) may be a reduced pressure that applies reduced pressure to tissue site 150 in the form of a triangular waveform varying between 25-125 mmHg with a rise time 212 set at a rate of +30 mmHg/min and a descent time 211 set at −30 mmHg/min. Again, the type of system and tissue site determines the type of reduced pressure therapy to be used.

Figure 3:
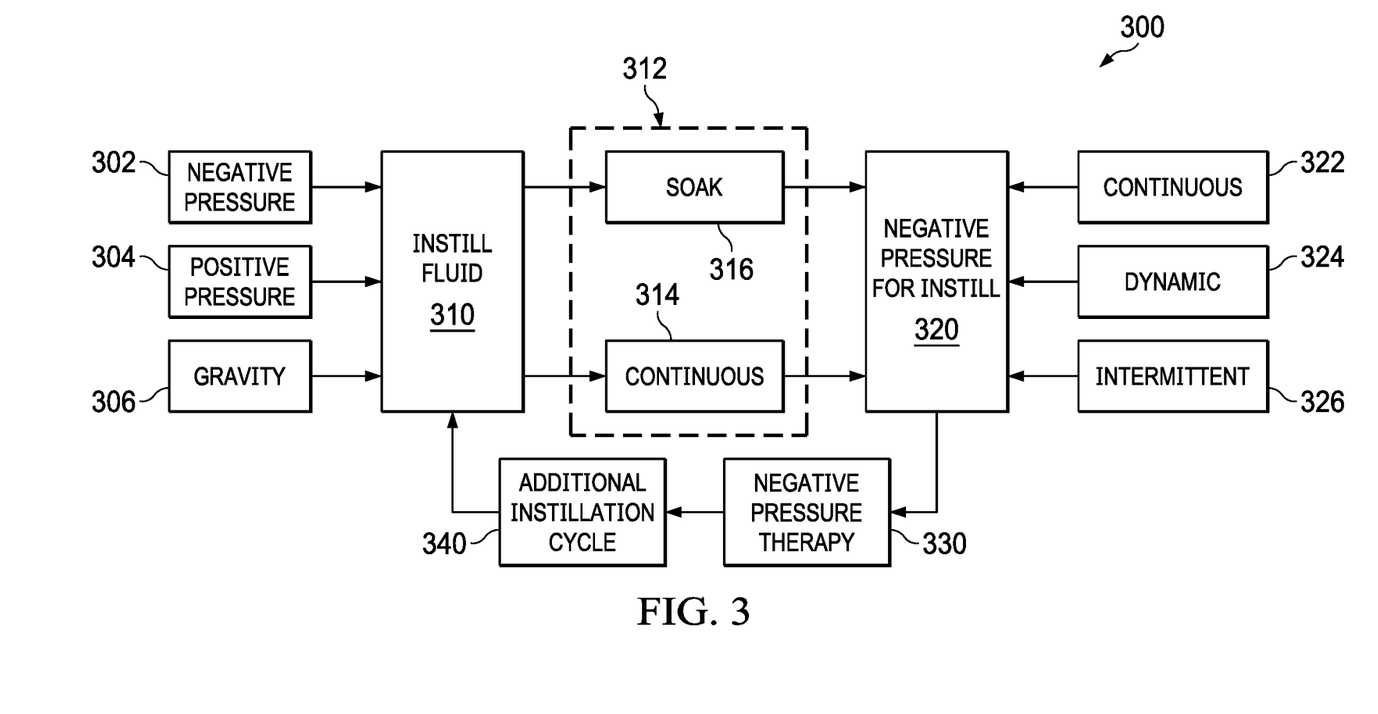
FIG. 3 is a flow chart showing an illustrative embodiment of a therapy method for providing negative-pressure and instillation therapy for delivering treatment solutions to a dressing at a tissue site.

FIG. 3 is a flow chart illustrating an illustrative embodiment of a therapeutic method 300 that may be used for providing negative-pressure and instillation therapy for delivering an antimicrobial solution or other treatment solution to a dressing at a tissue site. In one embodiment, the controller 110 receives and processes data, such as data related to fluids provided to the tissue interface. Such data may include the type of instillation solution prescribed by a clinician, the volume of fluid or solution to be instilled to the tissue site ("fill volume"), and the amount of time needed to soak the tissue interface ("soak time") before applying a negative pressure to the tissue site. The fill volume may be, for example, between 10 and 500 mL, and the soak time may be between one second to 30 minutes. The controller 110 may also control the operation of one or more components of the therapy system 100 to manage the fluids distributed from the solution source 114 for instillation to the tissue site 150 for application to the wound 152 as described in more detail above. In one embodiment, fluid may be instilled to the tissue site 150 by applying a negative pressure from the negative pressure source 104 to reduce the pressure at the tissue site 150 to draw the instillation fluid into the dressing 102 as indicated at 302. In another embodiment, fluid may be instilled to the tissue site 150 by applying a positive pressure from the negative pressure source 104 (not shown) or the separate positive pressure source 116 to force the instillation fluid from the solution source 114 to the tissue interface 108 as indicated at 304. In yet another embodiment, fluid may be instilled to the tissue site 150 by elevating the solution source 114 to height sufficient to force the instillation fluid into the tissue interface 108 by the force of gravity as indicated at 306. Thus, the therapy method 300 includes instilling fluid into the tissue interface 108 by either drawing or forcing the fluid into the tissue interface 108 as indicated at 310.

The therapy method 300 may control the fluid dynamics of applying the fluid solution to the tissue interface 108 at 312 by providing a continuous flow of fluid at 314 or an intermittent flow of fluid for soaking the tissue interface 108 at 316. The therapy method 300 may include the application of negative pressure to the tissue interface 108 to provide either the continuous flow or intermittent soaking flow of fluid at 320. The application of negative pressure may be implemented to provide a continuous pressure mode of operation at 322 as described above to achieve a continuous flow rate of instillation fluid through the tissue interface 108 or a dynamic pressure mode of operation at 324 as described above to vary the flow rate of instillation fluid through the tissue interface 108. Alternatively, the application of negative pressure may be implemented to provide an intermittent mode of operation at 326 as described above to allow instillation fluid to soak into the tissue interface 108 as described above. In the intermittent mode, a specific fill volume and the soak time may be provided depending, for example, on the type of wound 152 being treated and the type of dressing 102 being utilized to treat the wound 152. After or during instillation of fluid into the tissue interface 108 has been completed, the therapy method 300 may begin may be utilized using any one of the three modes of operation at 330 as described above. The controller 110 may be utilized to select any one of these three modes of operation and the duration of the negative pressure therapy as described above before commencing another instillation cycle at 340 by instilling more fluid at 310.

The therapy method 300 provides irrigation, i.e., the practice of washing out a wound or bodily opening with a stream of liquid solution, and lavage, i.e., the practice of washing out a cavity or organ, using a liquid solution for therapeutic purposes. Instilled fluid is slowly introduced into the wound and remains in the wound bed for a defined period of time before being removed by applying negative pressure as described above. Automated instillation helps with wound cleansing by loosening soluble contaminants in the wound bed followed by subsequent removal of infectious material during negative pressure therapy. As a result, soluble bacterial burden can be decreased, contaminants removed, and the wound thus cleansed, all without interaction from a user or clinician. The therapeutic method including therapeutic method 300 as generally described above (i) cleanses the wound with instillation of topical wound cleansers in a consistent, controlled manner, (ii) treats the wound with the instillation of appropriate topical antimicrobials and antiseptic solutions and the removal of infectious material, and (iii) heals the wound and prepares for primary or secondary closure of the wound.

Figure 4:
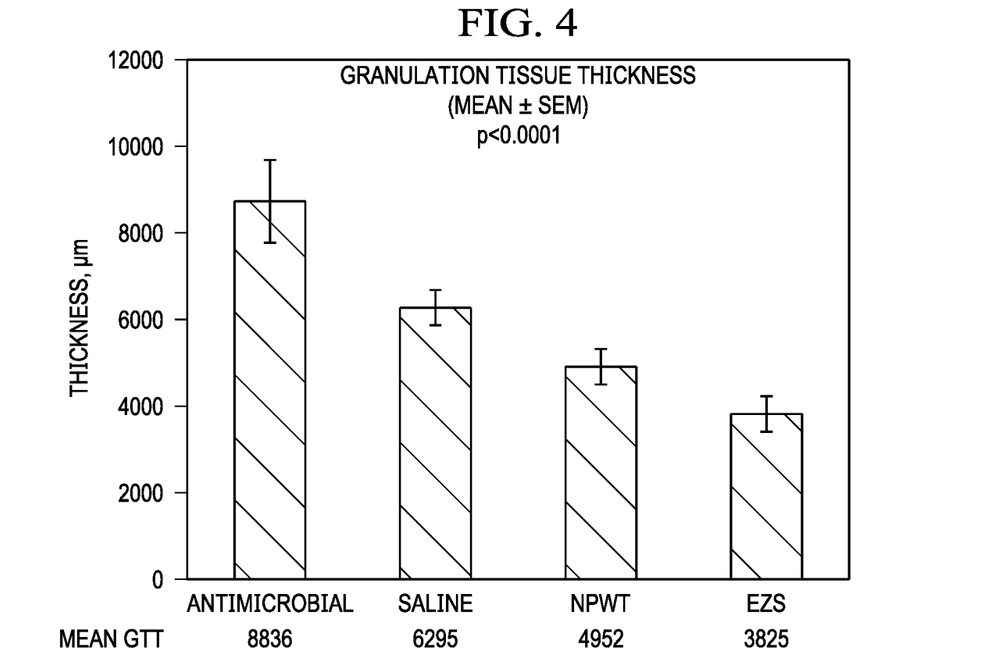
FIG. 4 is a bar chart illustrating the increase in granulation tissue thickness ("GTT") after (i) providing negative-pressure and instillation therapy for delivering instillation fluids to a dressing at a tissue site, (ii) providing such therapy using a saline solution, and (iii) providing such therapy using an antimicrobial that may be accomplished with the example embodiment of therapy system of FIGS. 1 and 1A in the therapy method of FIG. 3.

FIG. 4 is a bar chart illustrating the increase in granulation tissue thickness ("GTT") after (i) providing negative-pressure and instillation therapy for delivering instillation fluids to a dressing at a tissue site, (ii) providing such therapy using a saline solution, and (iii) providing such therapy using an antimicrobial that may be accomplished with the example embodiment of therapy system of FIGS. 1 and 1A in the therapy method of FIG. 3. Several preclinical studies have been conducted on animals utilizing the improved instillation technology as described above to determine the effect on granulation tissue formation. In one study, an in vivo porcine full-thickness wound model (n=12) was used to evaluate granulation tissue thickness. The therapy method included the following steps: (i) Each animal received contralateral 5 cm diameter full-thickness excisional dorsal wounds that were treated with the negative pressure and instillation therapy using the tissue interface and, more specifically, V.A.C. VeraFlo™ Therapy using the V.A.C. VeraFlo™ Dressing. (ii) The V.A.C. VeraFlo™ Therapy was set to instill 20 ml of normal saline, soak for 5 minutes and apply negative pressure of −125 mmHg continuously for 2.5 hours for 10 cycles per day. (iii) The V.A.C.® Therapy was set at −125 mmHg continuous pressure. (iv) After 7 days, tissue samples were processed for histology and stained with Masson's tri-chrome. (v) Granulation tissue thickness was measured from the base of the wound to the surface of the wound.

The results were quite unexpected and impressive. A significant increase in granulation thickness of about 43% (4.82±0.42 mm; p<0.05) was observed using the V.A.C. VeraFlo™ Therapy with V.A.C. VeraFlo™ Dressings compared to using only negative pressure therapy with the V.A.C.® GranuFoam™ Dressings (3.38±0.55 mm; p<0.05). Results of the histological findings showed that the increase in granulation thickness was the result of new tissue deposition, not swelling. Optimization of instillation and negative pressure therapy parameters, such as instillation volume, soak time, and cycle frequency may allow for further improvement in tissue granulation. However, it is uncertain how these swine results may correlate to human results.

Instillation and negative pressure therapy systems and methods are especially effective for improving tissue granulation when used in conjunction with antimicrobial solutions that have demonstrated efficacy against a broad range of healthcare-associated infections (HAIs), biofilms and planktonic microbes that are categorized and described above. Healthcare-associated infections, also known as hospital-acquired infections, include fungal, viral and bacterial infections that patients contract during the course of receiving healthcare treatment for other conditions. HAIs can cause severe pneumonia and infections of the urinary tract, bloodstream and other parts of the body. Some common HAIs include hospital-acquired pneumonia, Methicillin resistant *Staphylococcus aureus* (MRSA), *Clostridium difficile* spores, tuberculosis and gastroenteritis. These HAIs and biofilms survive on surfaces in the hospital and enter the body through wounds, catheters and ventilators, while the planktonic microbes survive in fluids associated with the tissue site.

To combat the growing threat of infections, antimicrobial solutions may be used as an instillation fluid in conjunction with the automated systems and methods described above including, for example, instilling the antimicrobial solutions to the tissue interface 108 in a continuous or intermittent mode followed by negative pressure therapy for treating the wound 152 at the tissue site 150.

Antimicrobial solutions comprising an antimicrobial agent containing a peroxy α-keto carboxylic acid as the active ingredient have demonstrated unique safety and efficacy properties that can mitigate or treat the increasing threat of HIAs, including the most resistant pathogens such as methicillin resistant *Staphylococcus aureus* (MRSA), CRE and *C. difficile* spores. Such antimicrobial agents are not only capable of destroying the bacteria that cause biofilms, but also capable of breaking down the biofilm matrix and reducing the total dry weight of the biofilm by almost 50% according to certain in vitro test results. One embodiment of an antimicrobial agent containing peroxy pyruvic acid as the active ingredient that may be utilized as an instillation fluid for the present therapeutic system and methods is the VERIOX™ antimicrobial agent available from CHD Bioscience of Fort Collins, Colorado. The VERIOX™ antimicrobial agent has demonstrated in preclinical animal studies its ability to disinfect and enhance the healing response in wounds, especially in conjunction with the instillation and negative pressure therapy systems and methods described above.

For example, an ex vivo study was undertaken using an instillation and negative pressure therapy method similar to the V.A.C. Ulta™ System available from Kinetic Concepts, Inc. of San Antonio, Texas, to determine how VERIOX™ antimicrobial agent, containing peroxy peruvic acid, performs on human wound pathogens. In this study, sponges that were used to remove debris from chronic infected wounds in human subjects were exposed to various concentrations of VERIOX™ and then tested for residual antimicrobial growth. VERIOX™ resulted in complete bacterial kill at 24-hours and 48-hours, post treatment, thus confirming the product's capability of destroying difficult-to-kill pathogens in a highly contaminated environment at low concentrations. Furthermore, the results were the same regardless of the wound type (diabetic, non-diabetic and drug-resistant wounds). This study demonstrated that antimicrobial solutions of the present technology can kill highly resistant pathogens (such as MRSA, CRE and *C. difficile* spores) without harming healthy cells or tissue at clinically efficacious levels.

In yet another example, an in vivo animal study was undertaken using an instillation and negative pressure therapy method similar to the V.A.C. Ulta™ System to treat a histomorphometry of porcine wounds with different antimicrobial solutions including the VERIOX™ antimicrobial agent as the instillation fluid. The results of this study are set forth in FIG. 4. This study demonstrates that the treatment not only did not harm healthy cells or tissue associated with the wound, but also greatly increased granulation tissue thickness by a remarkable 78% (8.836 mm; p<0.0001) over negative-pressure wound therapy without using the antimicrobial agent (4.952 mm; p<0.0001).

Without limiting the mechanism, function or utility of present technology, the systems and methods described herein may provide significant advantages relative to treatment modalities among those known in the art. For example, a single antimicrobial solution comprising peroxy pyruvic acid or other peroxy α-keto carboxylic acid may perform multiple functions in wound care thereby eliminating the serial healing method of debriding, washing with antiseptic, and granulation. Even though antimicrobial and/or antiseptic solutions used for wound cleansing may, in general, be toxic to cells at some level, the antimicrobial solution of the present technology comprising peroxy α-keto carboxylic acid combined with negative pressure therapy provides antimicrobial efficacy to kill biofilms and planktonic microbes while expediting granulation tissue growth. This single solution may also mitigate the need for a physician to frequently inspection the wound by removing the dressing to determine the next level of treatment and the timing of such treatments.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for treating a tissue site, comprising:
    a dressing including a tissue interface adapted to contact the tissue site and a cover adapted to provide a fluid seal between a therapeutic environment including the tissue interface proximate one side of the cover and a local external environment on the other side of the cover;
    a positive-pressure source operable to fluidly couple to a solution source, the positive-pressure source adapted to actuate the solution source for delivering an antimicrobial solution comprising a peroxy α-keto carboxylic acid having a concentration of 0.04% to the tissue interface; and
    a negative-pressure source fluidly coupled to the dressing and adapted to provide negative pressure to the therapeutic environment after delivery of the antimicrobial solution to the therapeutic environment.

2. The system according to claim 1, wherein the negative-pressure source is further adapted to provide negative pressure to the therapeutic environment before, during or after delivery of the antimicrobial solution to the therapeutic environment.

3. The system according to claim 1, further comprising a processor operatively coupled to the negative-pressure source to provide a target pressure to the therapeutic environment in a pressure control mode.

4. The system according to claim 3, wherein the pressure control mode is a continuous pressure mode.

5. The system according to claim 3, wherein the pressure control mode is an intermittent pressure mode.

6. The system according to claim 1, further comprising a processor operatively coupled to the negative-pressure source, the processor configured to operate the negative-pressure source to provide a variable target pressure to the therapeutic environment in a dynamic pressure mode.

7. The system according to claim 1, further comprising a processor operatively coupled to the positive-pressure source, the processor configured to operate the positive-pressure source to provide the antimicrobial solution to the therapeutic environment in a predetermined dosage.

8. The system according to claim 1, further comprising a processor operatively coupled to the positive-pressure source, the processor configured to operate the positive-pressure source to provide the antimicrobial solution to the therapeutic environment for a predetermined time.

9. The system according to claim 1, further comprising a processor operatively coupled to the positive-pressure source, the processor configured to operate the positive-pressure source to provide the antimicrobial solution to the therapeutic environment at a predetermined rate over time.

10. The system according to claim 1, further comprising a processor operatively coupled to the negative-pressure source and the positive-pressure source, the processor configured to operate the negative-pressure source and the positive-pressure source to provide negative pressure to the therapeutic environment prior to providing the antimicrobial solution to the therapeutic environment.

11. The system according to claim 1, further comprising a processor operatively coupled to the negative-pressure source and the positive-pressure source, the processor configured to operate the negative-pressure source and the positive-pressure source to provide negative pressure to the therapeutic environment after providing the antimicrobial solution to the therapeutic environment.

12. The system according to claim 1, further comprising a processor operatively coupled to the negative-pressure source and the positive-pressure source, the processor configured to operate the negative-pressure source and the positive-pressure source to provide negative pressure to the therapeutic environment while providing the antimicrobial solution to the therapeutic environment.

13. The system according to claim 1, further comprising a processor operatively coupled to the negative-pressure source and the positive-pressure source, the processor configured to operate the negative-pressure source and the positive-pressure source to provide negative pressure to the therapeutic environment and to provide the antimicrobial solution to the therapeutic environment, wherein at least one of the negative pressure and the antimicrobial solution are provided in a repeating manner.

14. The system according to claim 1, wherein the peroxy α-keto carboxylic acid is peroxy pyruvic acid.

15. The system according to claim 1, wherein the tissue interface is a manifold comprising a porous foam material having interconnected pores for distributing the antimicrobial solution to the therapeutic environment.

* * * * *